(12) United States Patent
Larson et al.

(10) Patent No.: US 11,926,408 B2
(45) Date of Patent: Mar. 12, 2024

(54) FAILSAFE VALVE FOR GEARED ROTARY ACTUATOR

(71) Applicant: MOOG INC., Elma, NY (US)

(72) Inventors: Lowell Van Lund Larson, Huntington Beach, CA (US); Robert Justin Sielaff, Holland, NY (US)

(73) Assignee: Moog Inc., Elma, NY (US)

( * ) Notice: Subject to any disclaimer, the term of this patent is extended or adjusted under 35 U.S.C. 154(b) by 416 days.

(21) Appl. No.: 17/420,432

(22) PCT Filed: Jan. 27, 2020

(86) PCT No.: PCT/US2020/015227
§ 371 (c)(1),
(2) Date: Jul. 2, 2021

(87) PCT Pub. No.: WO2020/209924
PCT Pub. Date: Oct. 15, 2020

(65) Prior Publication Data
US 2022/0081103 A1 Mar. 17, 2022

Related U.S. Application Data

(60) Provisional application No. 62/797,927, filed on Jan. 28, 2019.

(51) Int. Cl.
*B64C 13/42* (2006.01)
*F15B 20/00* (2006.01)
*F15B 13/04* (2006.01)

(52) U.S. Cl.
CPC ............ *B64C 13/42* (2013.01); *F15B 20/002* (2013.01); *F15B 20/004* (2013.01);
(Continued)

(58) Field of Classification Search
CPC .................. F15B 20/002; F15B 20/004; F15B 2211/8623; F15B 2211/8633; F15B 2211/8752
See application file for complete search history.

(56) References Cited

U.S. PATENT DOCUMENTS 3,662,550 A  5/1972 Lichtfuss
4,043,125 A * 8/1977 Kubik ..................... F16H 61/40
60/905

(Continued)

FOREIGN PATENT DOCUMENTS

GB  2112967 A * 7/1983 ............. F15B 13/16

*Primary Examiner* — Thomas E Lazo
(74) *Attorney, Agent, or Firm* — Hodgson Russ LLP

(57) ABSTRACT

A failsafe vale provides "Hole-In-The-Wall" failsafe functionality for thin-wing aircraft control surface actuation systems having a geared rotary actuator powered by a hydraulic rotary motor. The failsafe valve is associated with the hydraulic rotary motor and mechanically connected to the control surface, and enables the flight control surface to return to an aerodynamically neutral failsafe position if electrical control and/or hydraulic pressure is lost. When the failsafe valve receives a normal command pressure from the hydraulic system, the valve is inactive and the actuation system operates normally. However, if there is a loss of electrical command capacity to control hydraulic valves and/or a loss of hydraulic pressure, the failsafe valve is activated and connects one of the motor hydraulic control lines to the case return line for the motor if the control surface is away from its failsafe position. Consequently, the control surface will be hydraulically powered or aerodynamically ratcheted to its failsafe position in the failure event.

16 Claims, 13 Drawing Sheets

(52) U.S. Cl.
CPC ............. *F15B 2013/0409* (2013.01); *F15B 2013/0413* (2013.01); *F15B 2211/3058* (2013.01); *F15B 2211/31547* (2013.01); *F15B 2211/31594* (2013.01); *F15B 2211/41581* (2013.01); *F15B 2211/7058* (2013.01); *F15B 2211/7107* (2013.01); *F15B 2211/8623* (2013.01); *F15B 2211/8633* (2013.01); *F15B 2211/8752* (2013.01); *F15B 2211/8757* (2013.01)

(56) References Cited

U.S. PATENT DOCUMENTS

| | | | |
|---|---|---|---|
| 4,449,442 A | 5/1984 | Ebbing et al. | |
| 4,533,097 A * | 8/1985 | Aldrich | B64C 13/42 91/509 |
| 4,805,515 A | 2/1989 | Kast | |
| 4,905,933 A * | 3/1990 | Ako | B64C 13/42 244/99.4 |
| 5,020,322 A * | 6/1991 | Schwarz | F15B 20/004 91/33 |
| 5,983,782 A * | 11/1999 | Lebrun | F15B 15/12 60/403 |
| 6,487,960 B1 | 12/2002 | Chatufale | |
| 7,607,611 B2 | 10/2009 | Wingett et al. | |
| 7,607,677 B1 | 10/2009 | Wingett et al. | |
| 9,227,612 B2 | 1/2016 | Oyama et al. | |
| 2004/0245386 A1 | 12/2004 | Huynh | |
| 2009/0242694 A1 | 10/2009 | Oyama | |
| 2011/0068221 A1 | 3/2011 | Recksieck et al. | |
| 2015/0060707 A1 | 3/2015 | Baasch et al. | |
| 2017/0023031 A1 | 1/2017 | Wildman | |
| 2017/0233064 A1 * | 8/2017 | McCormick | B64C 13/504 244/99.5 |
| 2018/0002028 A1 | 1/2018 | Polcuch | |

\* cited by examiner

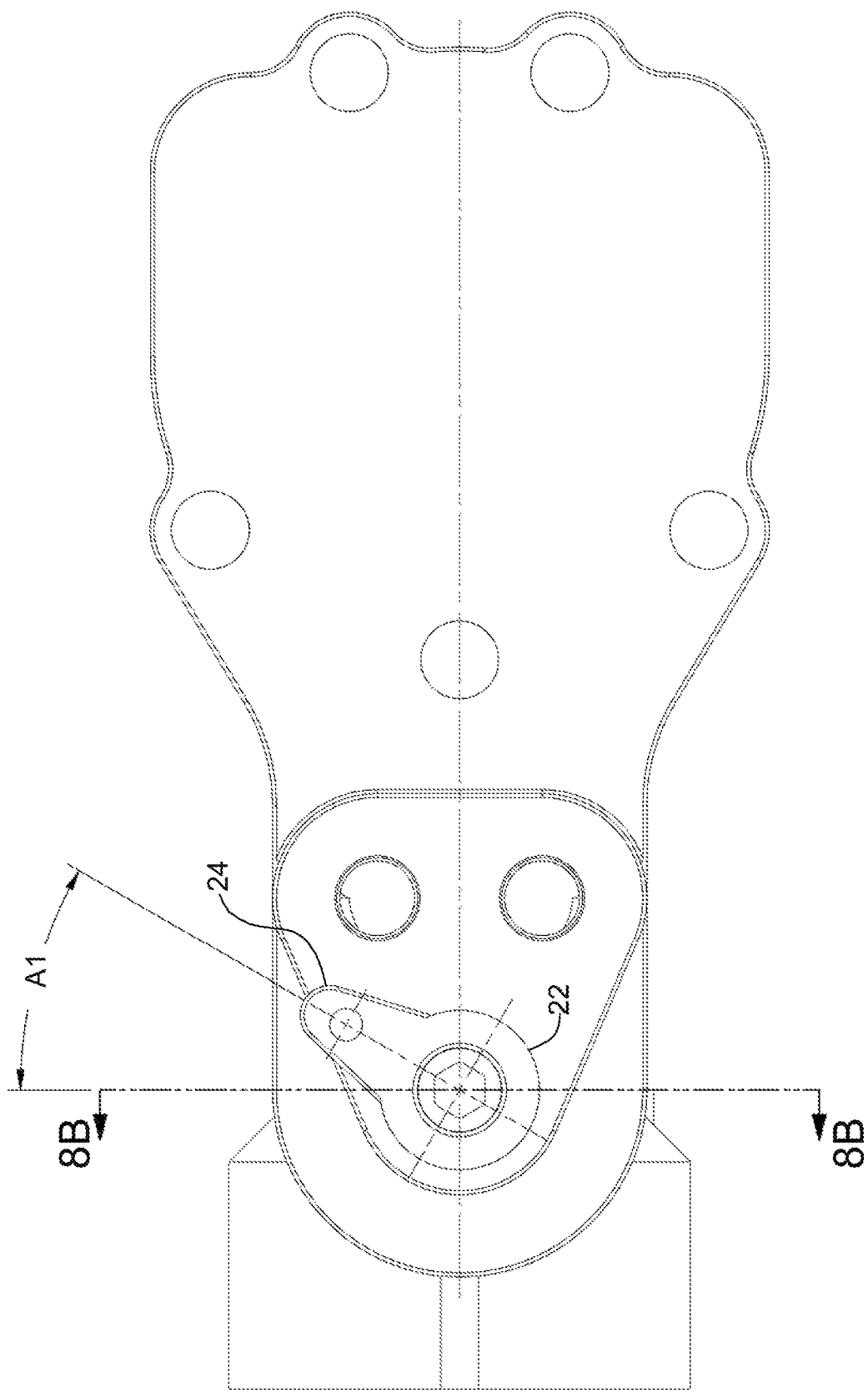

FAILSAFE VALVE FOR GEARED ROTARY ACTUATOR

CROSS-REFERENCE TO RELATED APPLICATIONS

The present application claims priority of U.S. provisional patent application No. 62/797,927 filed Jan. 28, 2019, the entire disclosure of which is incorporated herein by reference.

FIELD OF THE INVENTION

The present invention relates to failsafe operation of actuation systems such as actuation systems for aircraft control surfaces.

BACKGROUND OF THE INVENTION

In designing flight control actuation systems for positioning flight control surfaces of an aircraft, it is desirable that the control surface (e.g. a flap or a slat movably mounted on a fixed wing) be returned to and maintained in a neutral or centered "null" failsafe position in the event of a failure in the actuation system, for example loss of electrical power to electrically operated valves in the hydraulic circuit and/or loss of hydraulic pressure in the hydraulic circuit. Where the flight control actuation system relies on linear hydraulic actuators to move the control surfaces, centering of the control surface in failure mode has been accomplished in simple fashion. Linear hydraulic actuators have a piston within a cylinder chamber that divides the cylinder chamber into two chambers. To move the piston in a first axial direction, pressurized hydraulic fluid is delivered into the first chamber through a first control line (referred to herein as "P1"), and hydraulic fluid in the second chamber is allowed to flow out of the cylinder chamber through a second control line (referred to herein as "P2"), whereby the piston is displaced. As will be understood, the volume of the first chamber increases, and the volume of the second chamber decreases. Conversely, to move the piston in a second axial direction opposite the first axial direction, pressurized hydraulic fluid is delivered into the second chamber through the second control line P2, and hydraulic fluid in the first chamber is allowed to flow out of the cylinder chamber through the first control line P1. Centering of the control surface in failure mode has been accomplished in simple fashion using a "hole-in-the-wall" (HITW) port. The HITW port is provided through the wall of the hydraulic cylinder of the linear hydraulic actuator at an axial midpoint along the wall. When the linear hydraulic actuator is operating in its intended travel range under normal operating conditions, the HITW port is closed by the piston. However, if a failure event occurs, overtravel of the piston in one direction or the other will cause the HITW port to open on the high-pressure side of the piston so hydraulic fluid escapes to a hydraulic return line. Hydraulic pressure from the return line enables the hydraulic manifold to hydraulically fill the lower pressure side of the piston to force the piston of the linear hydraulic actuator toward a central null position in which the piston again blocks the HITW port and becomes hydraulically locked.

Hydraulic rotary motors, also referred to as rotary hydraulic actuators, operate in a manner analogous to linear hydraulic actuators, but have a rotor which rotates about and axis relative to a stator instead of a piston that moves linearly relative to a cylinder. A pair of hydraulic control lines P1 and P2 communicate by way of corresponding ports in the motor housing with respective variable chambers of the hydraulic rotary motor. To cause rotation of the rotor in a first direction, pressurized fluid is delivered to the motor by way of the first control line P1 and fluid is permitted to leave the motor by way of the second control line P2. To cause reverse rotation of the rotor in a second direction opposite the first direction, pressurized fluid is delivered to the motor by way of the second control line P2 and fluid is permitted to leave the motor by way of the first control line P1.

U.S. Pat. No. 5,983,782 to Lebrun et al. teaches an alternative version of the HITW concept adapted for a rotary hydraulic actuator as opposed to a linear hydraulic actuator. More specifically, Lebrun et al. disclose a rotary hydraulic actuator including an outer stator and an inner rotor having respective radial vanes for defining arcuate chambers each divided into two variable volume subchambers. The subchambers are connected to first and second control lines analogous to control lines P1 and P2 described above, and hydraulic flow may be selectively controlled in the control lines to cause the rotor to rotate relative to the stator in opposite first and second rotational directions. A HITW port, designated by reference numeral 22 in FIG. 1 of Lebrun et al., is provided in the stator to provide return pressure causing the rotor to rotate toward its null position in failsafe mode.

The HITW ports described above are provided through the stator or cylinder confining the pressurized working fluid. A drawback of the HITW ports described above is that the location of the port in the actuator, which determines the location of the null position during failsafe mode, is fixed and cannot be changed. Therefore, the null position of the hydraulic linear actuator or hydraulic rotary actuator cannot be readily adjusted after the actuator is manufactured, and the actuator is only suitable for specific applications having the designed null position.

Another disadvantage specific to the rotary hydraulic actuator disclosed by Lebrun et al. is that the range of rotary motion of the rotor relative to the stator is limited to an angle less than 360 degrees. Therefore, continuous revolutions of the rotor are not possible. Some aircraft have a need to use thin wings to reduce drag, thus requiring very thin (i.e. low height) trailing edge control surfaces driven by geared rotary actuators (GRAs) instead of conventional linear hydraulic actuators. The geared rotary actuators are directly attached to the control surface hinge axis, and a hydraulic rotary motor is located on the same axis to drive the GRA continuously through multiple revolutions. The rotary hydraulic actuator taught by Lebrun et al. is not suitable for this type of application due to its limited range of angular motion. While the use of GRAs helps to reduce aerodynamic drag, heretofore there has been no way to provide a HITW feature for fail-safe balancing of the control surface at a null failsafe position.

SUMMARY OF THE DISCLOSURE

The present disclosure has utility in actuation systems in which a movable member is actuated using hydraulic power supplied by a hydraulic rotary motor instead of a hydraulic linear actuator. In one application, the movable member is a flight control surface actuated relative to a fixed wing by a GRA powered by a hydraulic rotary motor. The present disclosure provides the same HITW function of returning the flight control surface to an aerodynamically neutral or null failsafe position in a failure event, without the need for a fixed port in the working hydraulic motor. The failure event may be, for example, the loss of electrical command capability for controlling the hydraulic manifold and/or the loss of hydraulic pressure.

In accordance with an embodiment of the present disclosure, a failsafe valve is associated with a hydraulic rotary motor powering the GRA, and is also mechanically connected to the control surface. When the failsafe valve receives a normal command pressure from the hydraulic flight control system, the failsafe valve is inactive and the flight control system operates in a normal mode. However, if there is a loss of hydraulic command pressure to the failsafe valve, the failsafe valve is activated and connects one of the motor hydraulic control lines (i.e. P1 or P2) to the case return line R for the hydraulic rotary motor if the control surface is away from its null or neutral failsafe position. As a result, the control surface will be hydraulically powered or aerodynamically ratcheted to its failsafe position in a failure event.

The failsafe valve may include a metering spool directly or indirectly connected to the control surface such that a rotational or axial position of the metering spool is determined by the position of the control surface relative to the fixed member, wherein the metering spool has a null position corresponding to the failsafe position of the movable member. When the metering spool is displaced from its null position in a first direction, the failsafe valve places the first control line P1 in communication with the drain return line R. Conversely, when the metering spool is displaced from its null position in a second and opposite direction, the failsafe valve places the second control line P2 in communication with the drain return line R.

Unlike the solution offered by Lebrun et al., the hydraulic rotary motor powering the GRA is free to operate through multiple revolutions because there is no angular limit imposed by a physical HITW in the hydraulic rotary motor. Moreover, the failsafe position of the control surface or other movable member may be easily changed for different applications by reconfiguring a transmission mechanism by which the movable member is connected to the metering spool.

BRIEF DESCRIPTION OF THE DRAWINGS

The nature and mode of operation of disclosed embodiments will now be more fully described in the following detailed description taken with the accompanying drawing figures, in which:

FIG. 8A is an end view of the failsafe valve, wherein the metering spool is displaced away from its null position in a first displacement direction;

DETAILED DESCRIPTION OF THE INVENTION

Figure 1A:
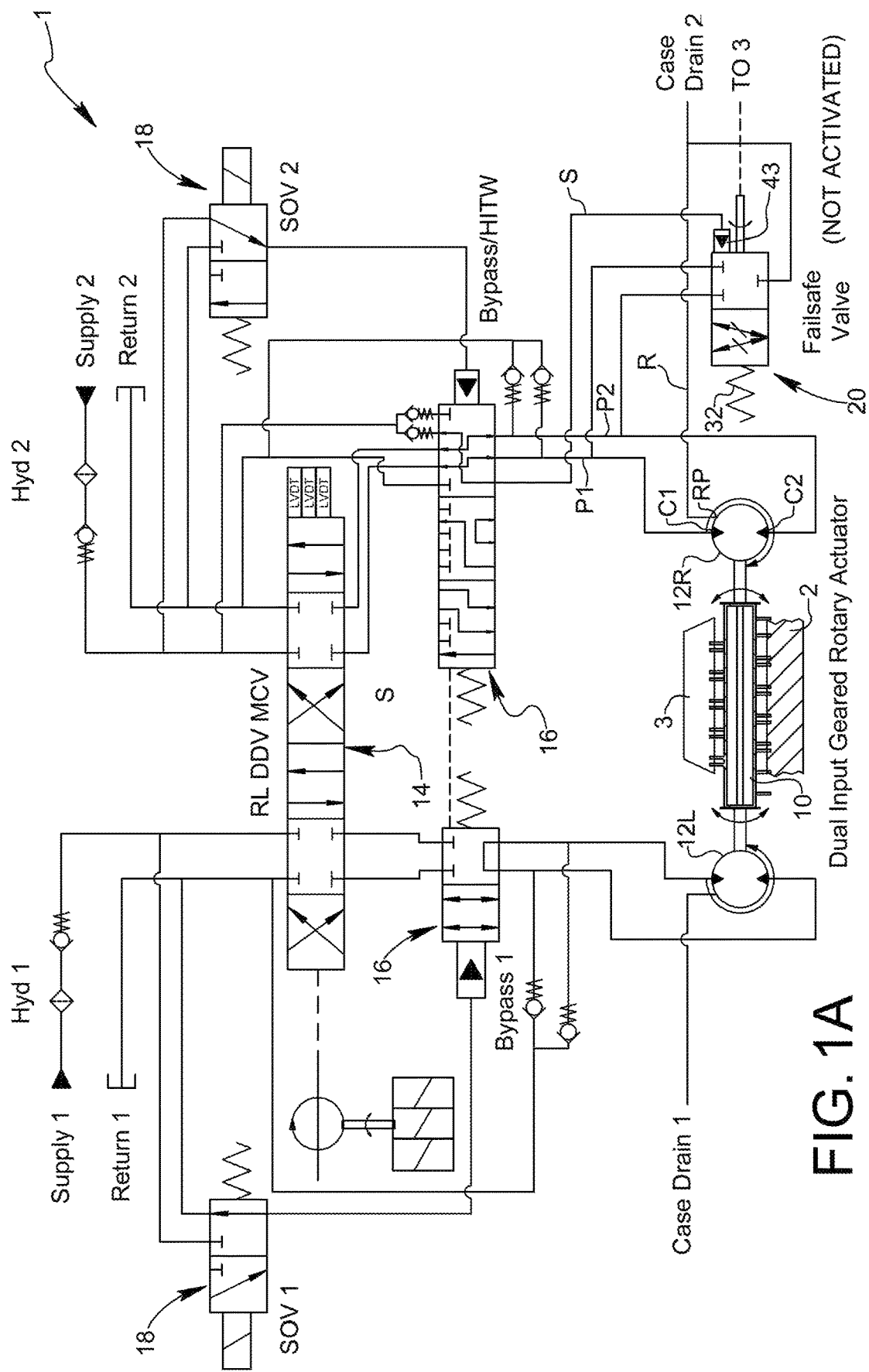
FIG. 1A is schematic view of a hydraulic flight actuation system incorporating a failsafe valve in accordance with an embodiment of the present disclosure, wherein the failsafe valve is shown in a non-activated state.
Figure 1B:
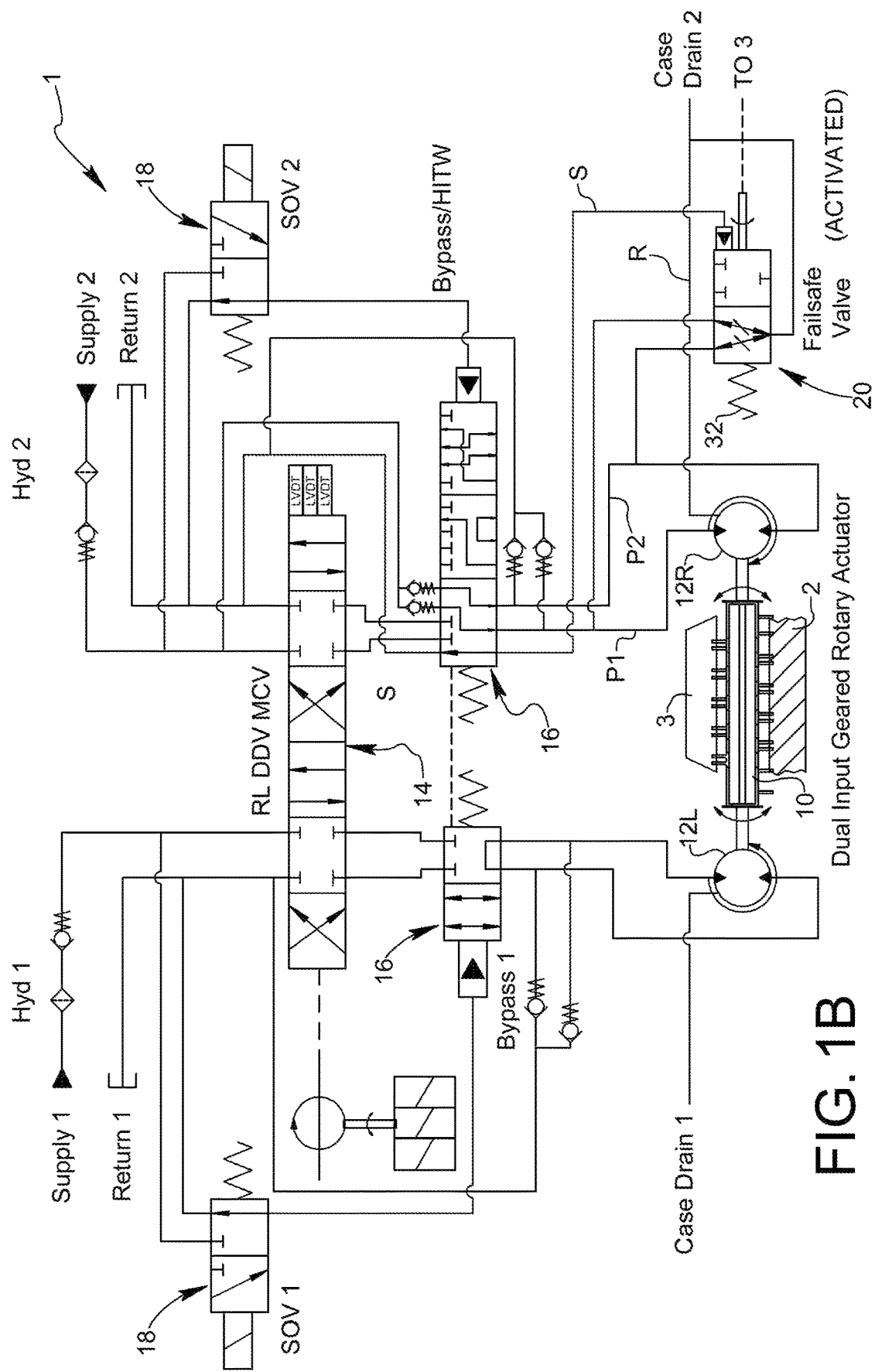
FIG. 1B is schematic view similar to that of FIG. 1A, wherein the failsafe valve is shown in an activated state.
Figure 2:
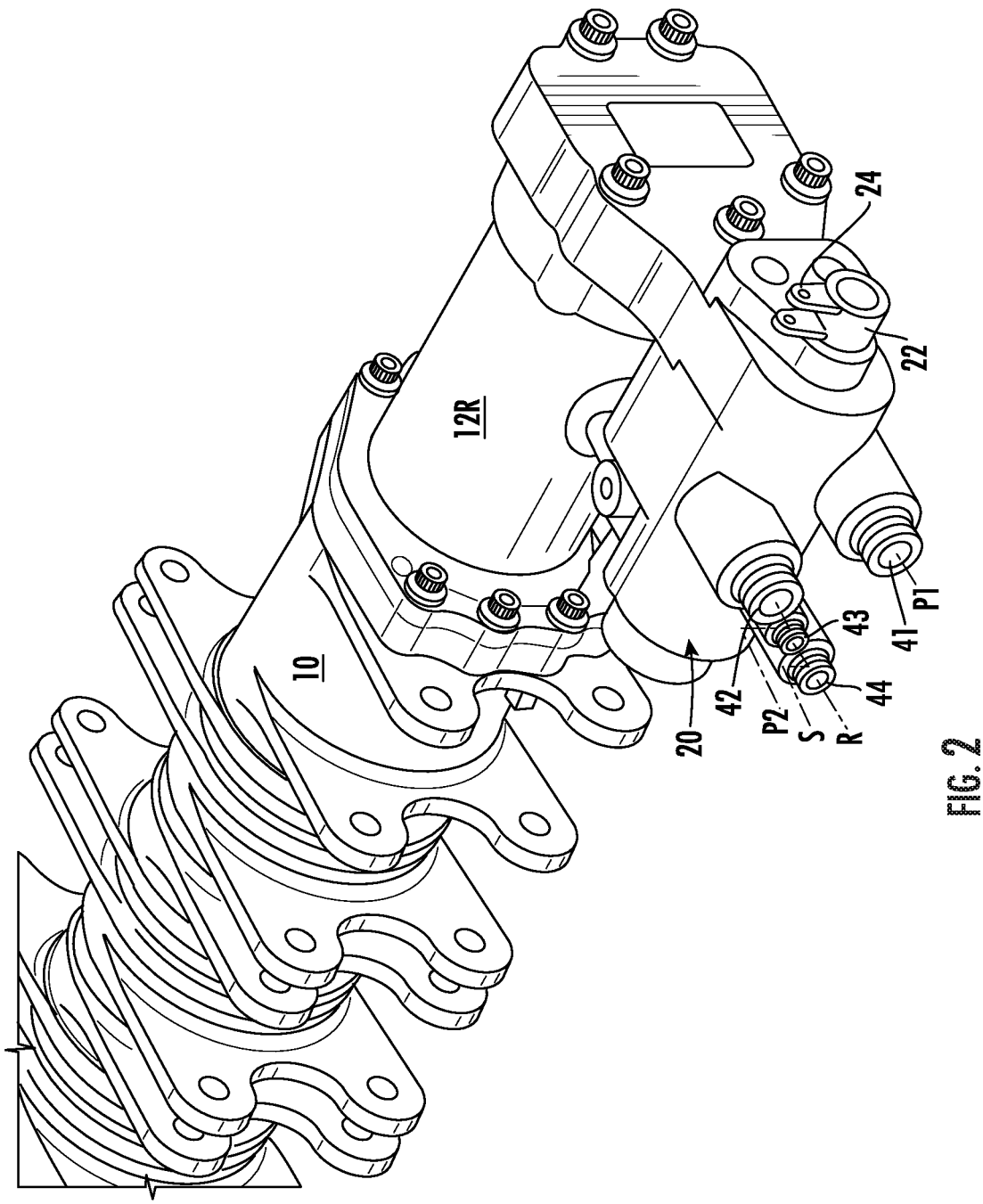
FIG. 2 is a perspective view showing the failsafe valve assembled in association with a hydraulic rotary motor and a geared rotary actuator (GRA) driven by the hydraulic rotary motor.
Figure 3:
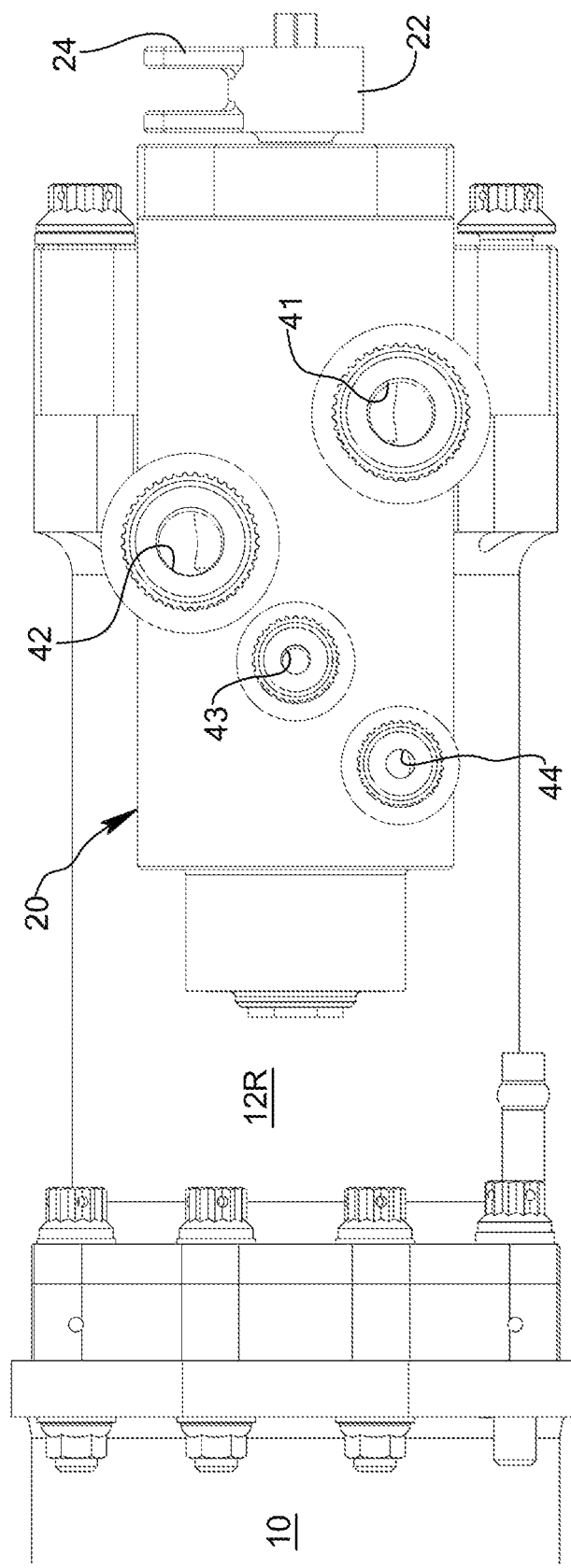
FIG. 3 is an elevational view of the failsafe valve, the hydraulic rotary motor, and a portion of the GRA.

FIGS. 1A and 1B schematically illustrate a hydraulically-powered flight control actuation system 1 for actuating a control surface of an aircraft, for example a flap or slat 3 connected to a fixed wing 2 of the aircraft by a geared rotary actuator (GRA) 10. GRA 10 may be a single input GRA driven by a single hydraulic rotary motor, or a dual input GRA driven by a pair of hydraulic rotary motors 12L and 12R as shown in FIGS. 1A and 1B. Hydraulic rotary motors 12L, 12R may be controlled by a hydraulic system including a main control valve 14, bypass valves 16, and shut-off valves 18. For example, the hydraulic system may be a dual redundant system including a first hydraulic subsystem designated Hyd 1 for controlling hydraulic rotary motor 12L at the left end of GRA 10, and a second hydraulic subsystem Hyd 2 controlling the other hydraulic rotary motor 12R at the right end of GRA 10. More specifically, second hydraulic subsystem Hyd 2 includes a first hydraulic control line P1 in hydraulic communication with a first control port C1 of hydraulic rotary motor 12R, a second hydraulic control line P2 in hydraulic communication with a second control port C2 of hydraulic rotary motor 12R, and a case drain return line R in hydraulic communication with a return port RP of hydraulic rotary motor 12R.

In accordance with the present disclosure, at least one of the hydraulic motors 12L, 12R and control surface 3 are connected to a failsafe valve 20. In FIGS. 1A and 1B, only one failsafe valve 20 is shown in association with hydraulic motor 12R on the right end of GRA 10, however it will be understood that another failsafe valve may be provided in association hydraulic motor 12L on the left end of GRA 10.

In FIG. 1A, failsafe valve 20 is shown in its non-activated state. When failsafe valve 20 is in its non-activated state, the hydraulic flight control actuation system 1 is operating normally and failsafe valve 20 plays no role. In FIG. 1B, failsafe valve 20 is shown in its activated state, meaning that the hydraulic flight control actuation system has experienced a failure causing loss of hydraulic pressure to hydraulic rotary motor 12R. In its activated state, failsafe valve 20 connects an appropriate one of the hydraulic control lines P1 or P2 for hydraulic motor 12R to case drain return line R for the hydraulic motor if the control surface 3 is not at its aerodynamically null or neutral failsafe position, thereby allowing the control surface 3 to move to its failsafe position.

FIGS. 2-7 show one possible arrangement of failsafe valve 20 and hydraulic rotary motor 12R. As may be seen, the hydraulic control lines P1 and P2 of second hydraulic subsystem Hyd 2 connect respectively to a first control port 41 and a second control port 42 in a housing 21 of failsafe valve 20, a hydraulic supply line S of second hydraulic subsystem Hyd 2 connects to a command port 43 in valve housing 21, and case drain return line R of second hydraulic subsystem Hyd 2 connects to a return port 44 in the valve housing. In the depicted embodiment, failsafe valve 20 may include a first control conduit 51 communicating with first control port 41 and with first control port C1 of hydraulic motor 12R, a second control conduit 52 communicating with second control port 42 and with second control port C2 of hydraulic motor 12R, and a return conduit 54 communicating with return port 44 and with return port RP of hydraulic motor 12R. Thus, command port 43 is in hydraulic communication with hydraulic supply line S, first control conduit 51 is in hydraulic communication with first hydraulic control line P1 and first control port C1 of hydraulic rotary motor 12R, second control conduit 52 is in hydraulic communication with second hydraulic control line P2 and second control port C2 of hydraulic rotary motor 12R, and return conduit 54 is in hydraulic communication with the hydraulic return line R and the return port RP of hydraulic rotary motor 12R.

Failsafe valve 20 may include a valve arm 22 protruding from one end of valve housing 21. Valve arm 22 may include a clevis 24 on its protruding portion for connection to a transmission mechanism (not shown) connected to control surface 3. Movement of control surface 3 about a hinge axis 11 of GRA 10 may be transmitted to valve arm 22 by way of the transmission mechanism, thereby causing valve arm 22 to rotate about its longitudinal axis relative to the housing of failsafe valve 20. An example of a transmission mechanism is shown and described below in connection with FIG. 10. Instead of using an intervening transmission mechanism, valve arm 22 may be directly connected to control surface 3.

Figure 4:
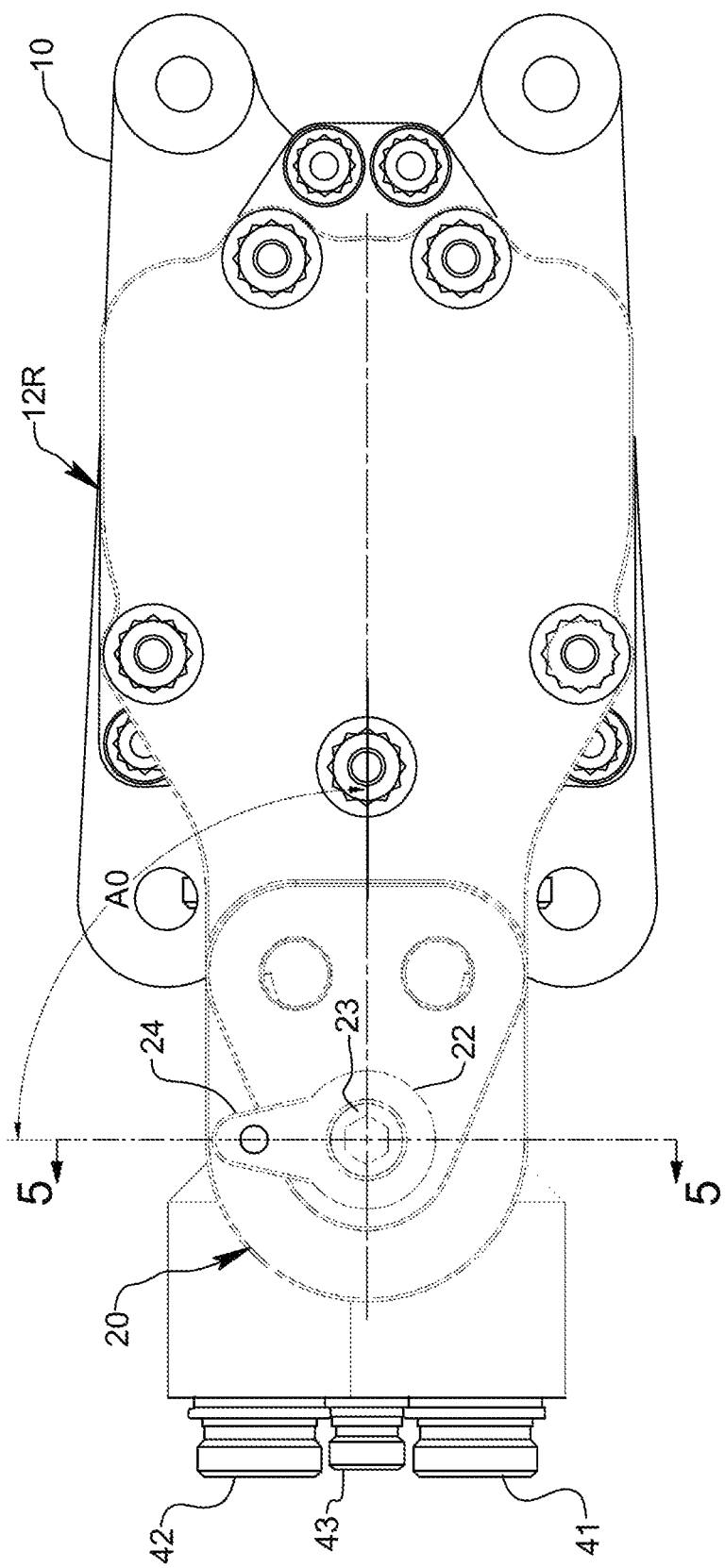
FIG. 4 is an end view of the failsafe valve, the hydraulic rotary motor, and the GRA.

Failsafe valve 20 may include a shaft 23 defining a central axis 25 about which valve arm 22 rotates. A metering spool 26 may be housed within a valve sleeve 28 and coupled to valve arm 22 to rotate with valve arm 22 about axis 25 of shaft 23. The rotation of metering spool 26 about valve axis 25 is relative to valve sleeve 28, which remains in a fixed position within valve housing 21. Metering spool 26 may be keyed to a slotted command spool 30 slidably mounted on an end of metering spool 26. A spring 32 engages a plugged end of housing 21 and biases command spool 30 in an axial direction to the left in FIGS. 5 and 7. In FIGS. 2-7, valve arm 22 and metering spool 26 are shown at a null rotational position A0 corresponding to a failsafe position of control surface 3. In the depicted embodiment, the null rotational position A0 of metering spool 26 is characterized by clevis 24 extending in a vertical direction, as best seen in FIG. 4.

Failsafe valve 20 is configured such that hydraulic communication is possible between first control conduit 51 and return conduit 54, or between second control conduit 52 and return conduit 54, but only when the failsafe valve is in its activated state. For example, metering spool 26 and valve sleeve 28 may define respective passageways 61 and 71, such that as metering spool 26 is rotated in a first rotational direction about valve axis 25 away from the null rotational position A0, passageways 61 in metering spool 26 will move into overlapped communication with passageways 71 in valve sleeve 28, thereby allowing hydraulic fluid to flow from first control conduit 51 to return conduit 54 as described in greater detail below with reference to FIG. 8B.

Similarly, when metering spool 26 is rotated in a second rotational direction about valve axis 25 opposite the first rotational direction and away from the null rotational position A0, passageways 62 in metering spool 26 will move into overlapped communication with passageways 72 in valve sleeve 28, thereby allowing hydraulic fluid to flow from second control conduit 52 to return conduit 54 as described in greater detail below with reference to FIG. 9B. Hydraulic flow may reach return conduit 54 by way of a plurality of radial openings 74 through valve sleeve 28.

Figure 5:
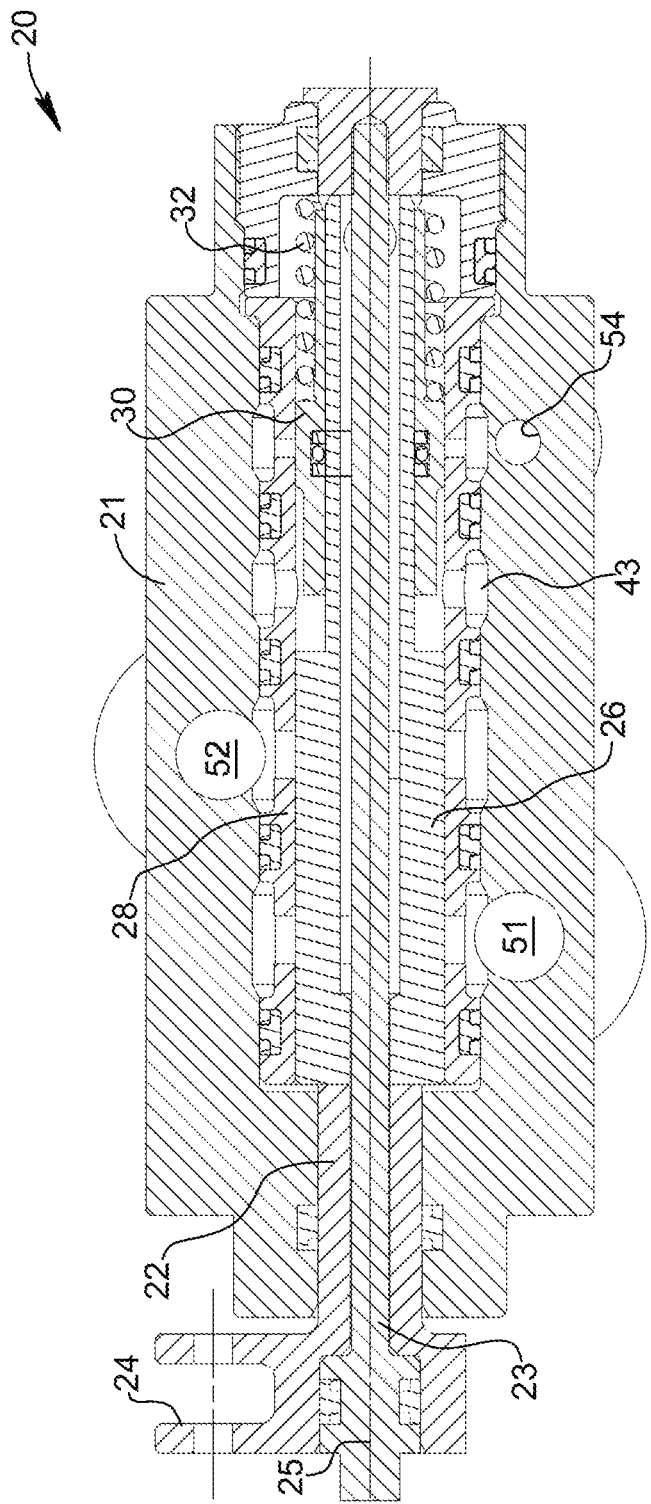
FIG. 5 is a cross-sectional view of the failsafe valve taken generally along the line 5-5 in FIG. 4, wherein the failsafe valve is in its non-activated state.
Figure 6:
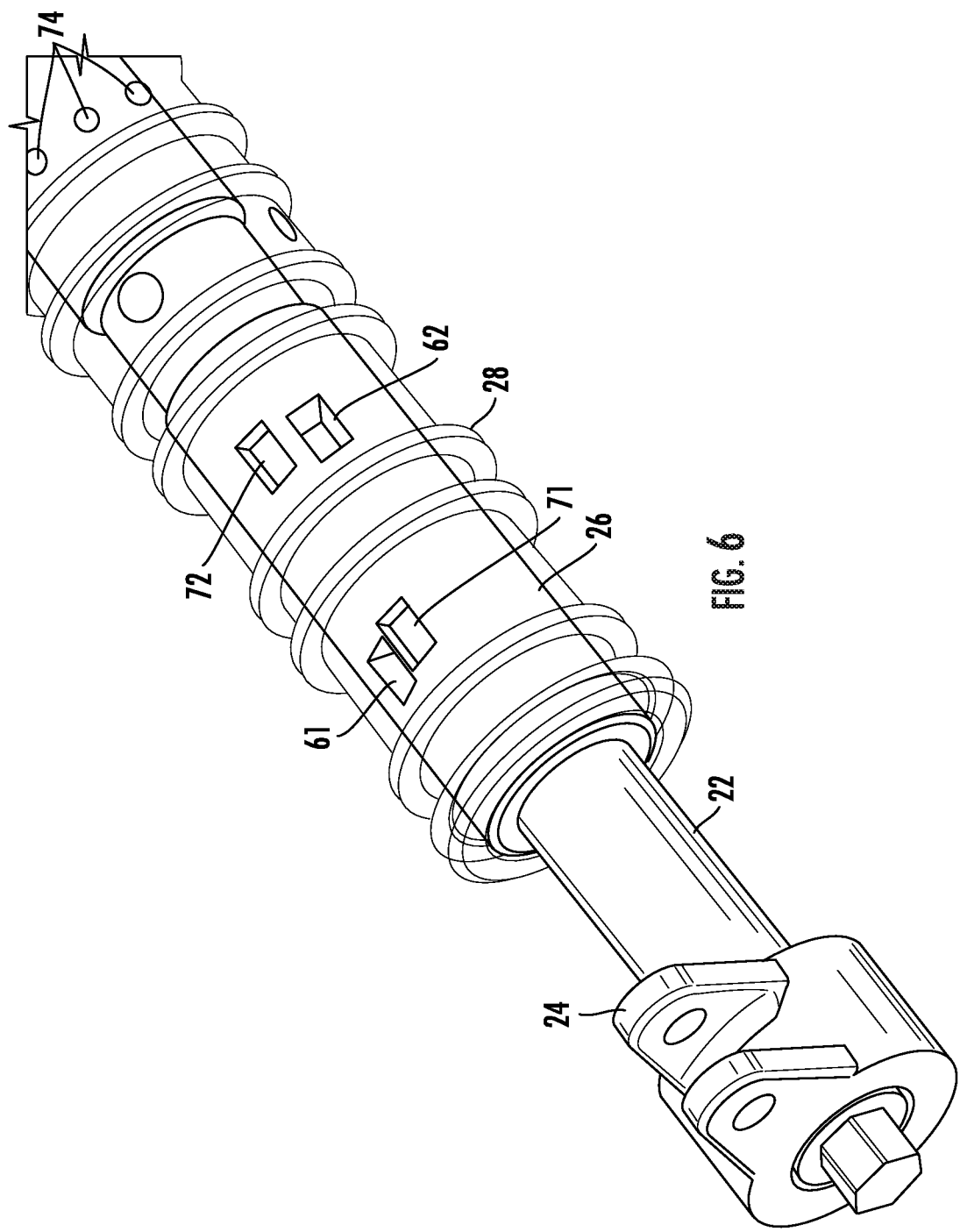
FIG. 6 is a perspective view, partially transparent, showing a valve arm, a sleeve, and a metering spool of the failsafe valve.
Figure 7:
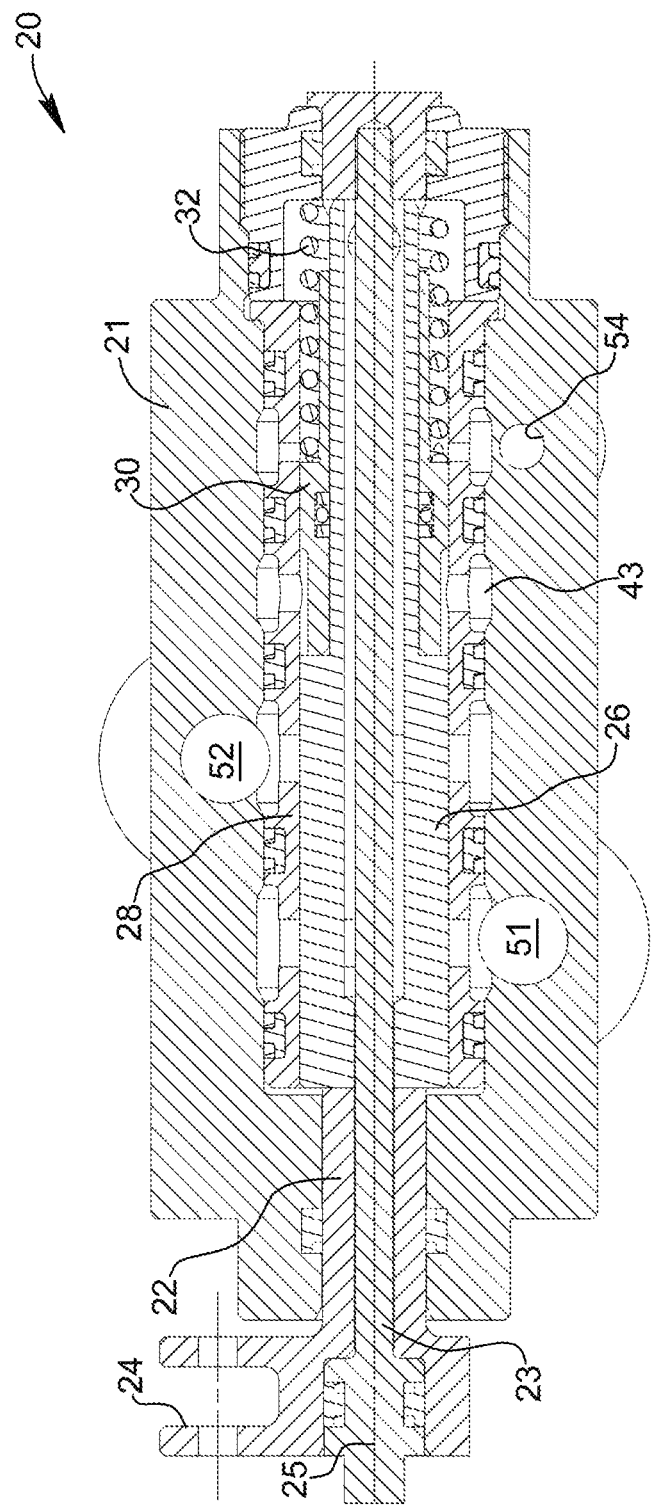
FIG. 7 is a cross-sectional view of the failsafe valve, wherein the failsafe valve is in its activated state and the metering spool and valve arm of the failsafe valve are at a null position thereof.

In FIG. 5, failsafe valve 20 is in its non-activated state, whereas in FIG. 7, failsafe vale 20 is in its activated state. The state of failsafe valve 20 may be determined by the axial position of command spool 30. When hydraulic pressure in hydraulic supply line S is greater than or equal to a predetermined normal pressure, the hydraulic pressure delivered through command port 43 is sufficient to force command spool 30 to the right in FIG. 5 against the bias of spring 32 such that command spool 30 blocks radial openings 74 leading to return conduit 54, thereby preventing hydraulic communication between first and second control conduits 51, 52 on the one hand, and return conduit 54 on the other. As will be understood, when hydraulic pressure in hydraulic supply line S is lost due to a malfunction or failure of second hydraulic subsystem Hyd 2 of the flight control actuation system, hydraulic pressure at command port 43 will decrease to less than the predetermined normal pressure, and spring 32 will displace command spool 30 axially to the left, as viewed in FIG. 7, to unblock radial openings 74 leading to return conduit 54 and place failsafe valve 20 in its activated state.

Reference is now made to FIGS. 8A, 8B, 9A, and 9B to further describe operation of failsafe valve 20 in its activated state. When failsafe valve 20 is in its activated state, the rotational position of metering spool 26 may determine which hydraulic control line, P1 or P2, is connected by the failsafe valve 20 to communicate with drain return line R. The rotational position of metering spool 26 may be determined by the angular position of control surface 3 to which metering spool 26 is connected by way of valve arm 22 and an intervening transmission mechanism, if any, between valve arm 22 and the control surface. As mentioned above, if control surface 3 is away from its failsafe position, failsafe valve 20 connects one of the hydraulic control lines P1 or P2 to drain return line R.

Figure 8B:
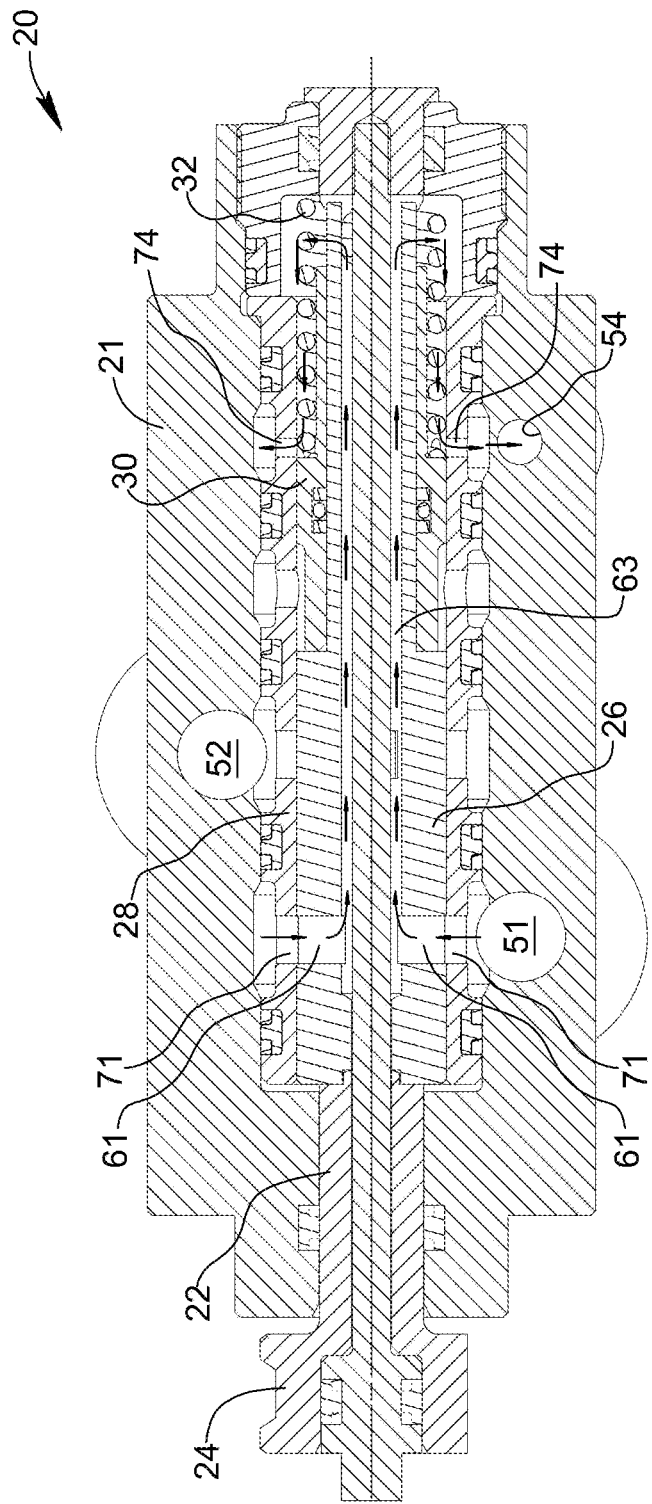
FIG. 8B is a cross-sectional view of the failsafe valve taken generally along the line 8B-8B in FIG. 8A, illustrating hydraulic flow.

In FIGS. 8A and 8B, metering spool 26 is rotated about valve axis 25 in the first rotational direction away from its null rotational position A0 such that hydraulic communication is opened between first hydraulic control line P1 and drain return line R. First control conduit 51, which communicates with first hydraulic control line P1 through first control port 41, hydraulically communicates through passageways 71 and 61 with an annular passageway 63 defined between shaft 23 and an internal diameter of metering spool 26. Annular passageway 63 may extend axially along the interior of failsafe valve 20 to an opening 65 of metering spool 26, allowing hydraulic fluid to travel out of passageway 63, into an annular space in which spring 32 is located, and through radial openings 74 in valve sleeve 28 to return conduit 54. From return conduit 54, hydraulic fluid travels through return port 44 to drain return line R.

Figure 9A:
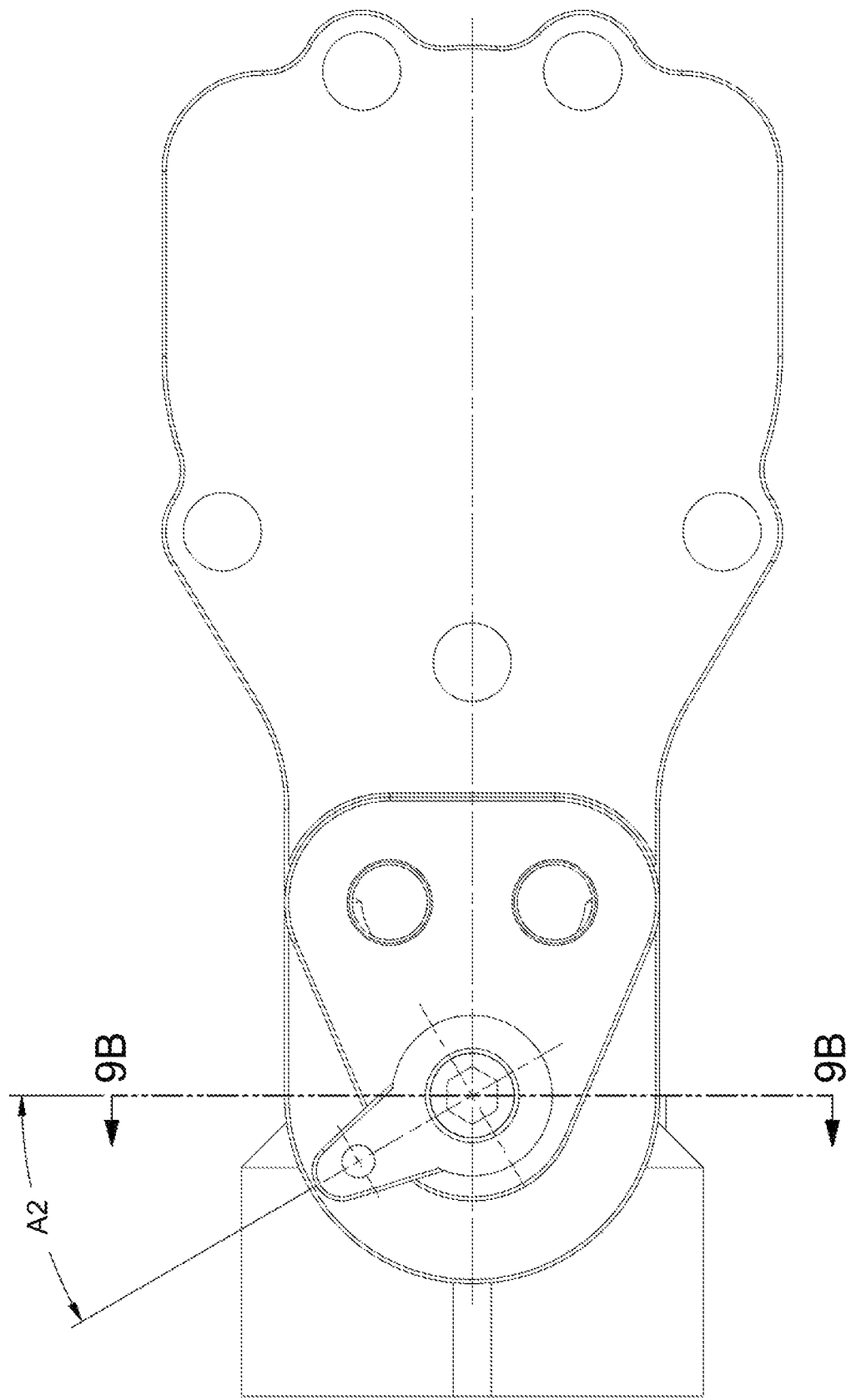
FIG. 9A is an end view of the failsafe valve, wherein the metering spool is is displaced away from its null position in a second displacement direction.
Figure 9B:
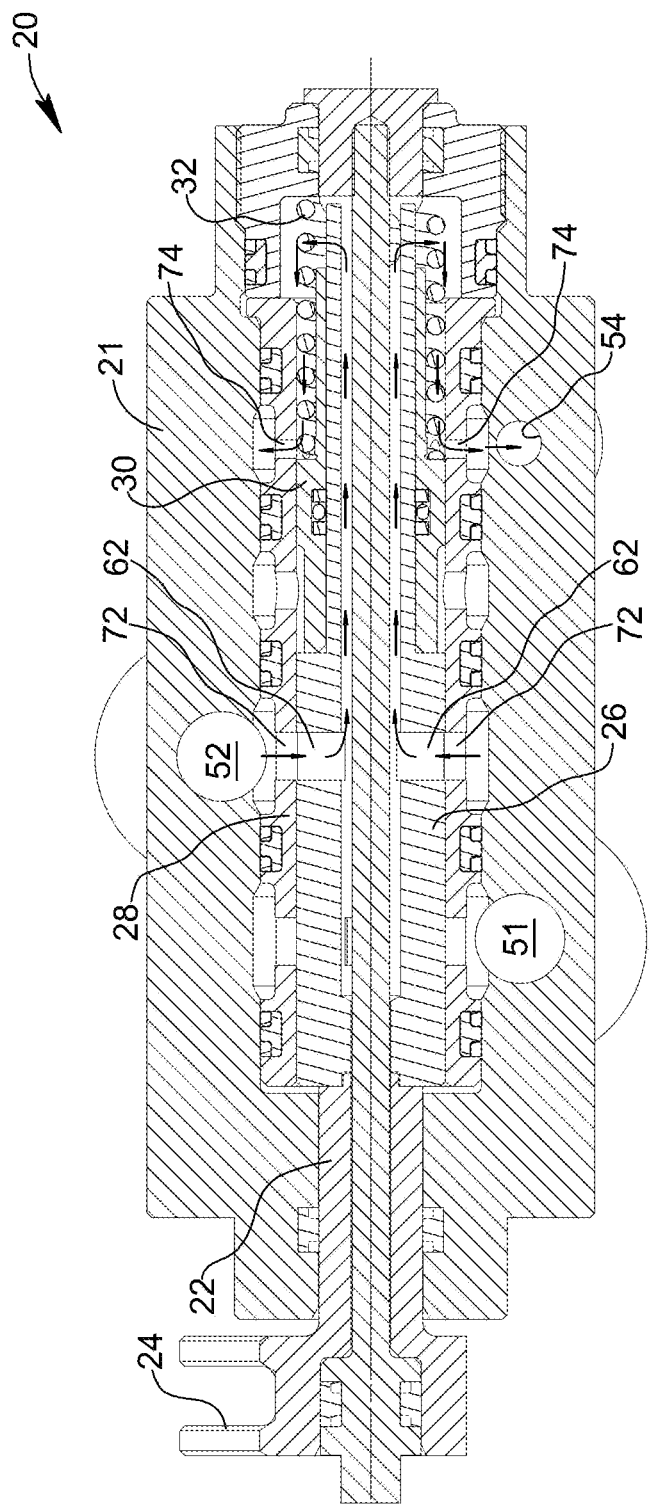
FIG. 9B is a cross-sectional view of the failsafe valve taken generally along the line 9B-9B in FIG. 9A, illustrating hydraulic flow.

In FIGS. 9A and 9B, metering spool 26 is rotated about valve axis 25 in the second rotational direction away from its null rotational position such that hydraulic communication is opened between second hydraulic control line P2 and drain return line R. Second control conduit 52, which communicates with second hydraulic control line P1 through second control port 42, hydraulically communicates with annular passageway 63 by way of passageways 72 and 62. As described above, annular passageway 63 leads to opening 65, allowing hydraulic fluid to travel out of passageway 63 and through radial openings 74 to return conduit 54. From return conduit 54, hydraulic fluid travels through return port 44 to drain return line R.

For example, if the second hydraulic subsystem Hyd 2 loses electrical supply when control surface 3 is tilted upward away from its failsafe position, then failsafe valve 20 will receive decreased pressure at command port 43 as the shut-off valve 18 of Hyd 2 goes from opened to closed without electrical power, and failsafe valve 20 will transition from its non-activated state to its activated state. Due to the position of valve arm 22 and metering spool 26, and the spaced arrangement of passageways 61 and 62, a flow passageway is opened whereby motor control pressure from second hydraulic control line P2 is directed to drain return line R and hydraulic motor 12R sees full system pressure from first hydraulic control line P1 at first control port C1, thus driving the hydraulic rotary motor to actuate control surface 3 toward its failsafe position. If control surface 3 is tilted downward away from its failsafe position, the reverse will happen, i.e. failsafe valve 20 may direct the motor control pressure from first hydraulic control line P1 to the drain return line R and hydraulic rotary motor 12R sees full system pressure from second hydraulic control line P2 at second control port C2, thus driving the motor to actuate the control surface 3 toward its failsafe position. Once control surface reaches its failsafe position from either direction, motor control pressures are equalized and porting to return line R is closed, whereby control surface 3 becomes hydraulically locked in its failsafe position.

As mentioned above, GRA 10 may be driven by a pair of hydraulic motors 12L and 12R. The following table represents various modes of the example system depicted in FIGS. 1A and 1B:

| Hyd 1 | Hyd 2 | Electric | Mode Hyd 1 | Mode Hyd 2 |
|---|---|---|---|---|
| on | on | On | active | active |
| on | off | On | active | bypass |
| off | on | On | bypass | active |
| off | off | On | bypass | ratchet to failsafe |
| off | off | Off | bypass | ratchet to failsafe |
| off | on | Off | bypass | power to failsafe |
| on | on | Off | bypass | power to failsafe |

When both the first and second hydraulic subsystems (Hyd 1 and Hyd 2) have hydraulic power, and there is electrical power to operate main control valve 14 and shut-off valves 18, then the flight control actuation system 1 will operate in its normal active mode to control the position of control surface 3.

If the first hydraulic subsystem Hyd 1 has hydraulic power but the second hydraulic subsystem Hyd 2 loses hydraulic power, and there is electrical power to operate main control valve 14 and shut-off valves 18, then flight control actuation system 1 will operate in a bypass mode in which first and second hydraulic control chambers of hydraulic rotary motor 12R are placed into hydraulic communication with one another such that hydraulic fluid can flow freely between the two chambers, allowing the fully functional first hydraulic subsystem Hyd 1 to actively drive GRA 10 by operation of hydraulic rotary motor 12L alone, with minimal resistance from hydraulic rotary motor 12R.

Conversely, if the second hydraulic subsystem Hyd 2 has hydraulic power but the first hydraulic subsystem Hyd 1 loses hydraulic power, and there is electrical power to operate main control valve 14 and shut-off valves 18, then flight control actuation system 1 will operate in a bypass mode in which first and second hydraulic control chambers of hydraulic rotary motor 12L are placed into hydraulic communication with one another such that hydraulic fluid can flow freely between the two chambers, allowing the fully functional second hydraulic subsystem Hyd 2 to actively drive GRA 10 by operation of hydraulic rotary motor 12R alone, with minimal resistance from hydraulic rotary motor 12L.

When both hydraulic subsystems lose hydraulic power, first hydraulic subsystem Hyd 1 will operate in bypass mode as described above. However, failsafe valve 20 will transition to its activated state such that second hydraulic subsystem 2 will allow control surface 3 to "ratchet" to its aerodynamically neutral failsafe position under aerodynamic loading. Hydraulic subsystems Hyd 1 and Hyd 2 will respectively operate in bypass and ratchet modes regardless of whether there is electrical power or not.

When second hydraulic subsystem Hyd 2 has hydraulic power but electrical power is lost, first hydraulic subsystem Hyd 1 will operate in bypass mode as described above. Failsafe valve 20 will transition to its activated state such that second hydraulic subsystem Hyd 2 will hydraulically power control surface 3 to its failsafe position. Hydraulic subsystems Hyd 1 and Hyd 2 will respectively operate in bypass and power-to-failsafe modes regardless of whether first hydraulic subsystem Hyd 1 has hydraulic power or not.

Figure 10:
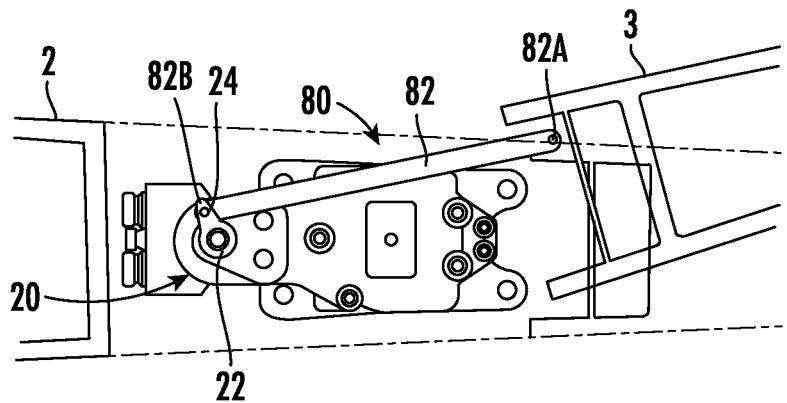
FIGS. 10, 11, and 12 are schematic side views illustrating one possible transmission mechanism between the control surface and the failsafe valve.
Figure 11:
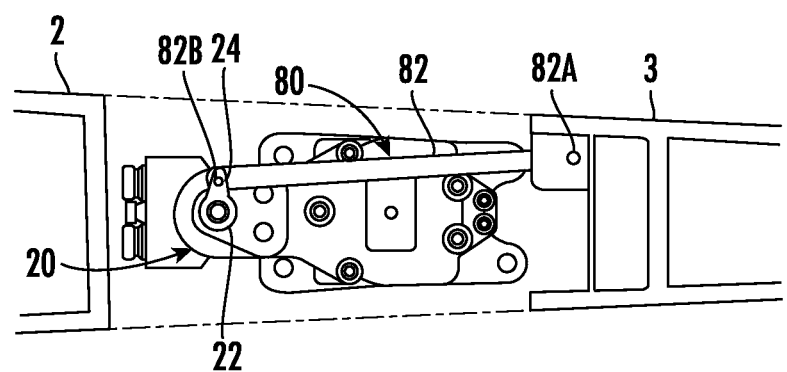
Figure 12:
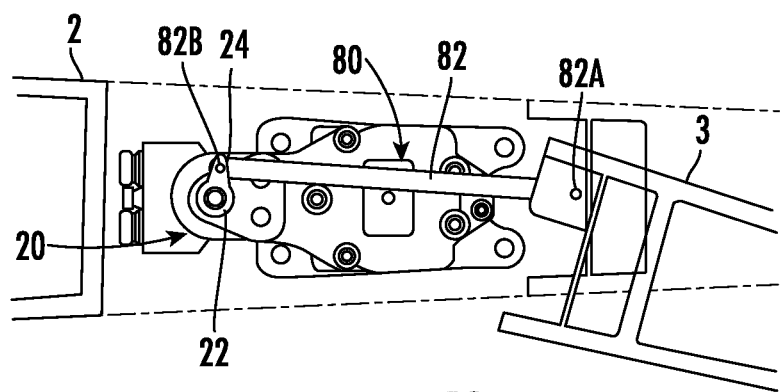

The connection of metering spool 26 and valve arm 22 to control surface 3 may be designed kinematically such that the failsafe position of control surface 3 corresponds to the null position of metering spool 26. For example, as shown in FIGS. 10-12, a transmission mechanism 80 mechanically couples control surface 3 to valve arm 22 (and thus to metering spool 26) such that when control surface 3 is at its aerodynamically neutral position shown in FIG. 11, metering spool 26 is caused to be in its null position. As illustrated by the depicted embodiment, the failsafe position of control surface 3 may be an intermediate, for example centered, angular position of control surface 3 in its range of pivotal motion about axis 11 of GRA 10. Transmission mechanism 80 may be configured to displace valve arm 22 and metering spool 26 in first and second opposite directions away from its null position depending on the direction of displacement of control surface 3 away from its failsafe position. Consequently, in the illustrated embodiment, transmission mechanism 80 displaces valve arm 22 and metering spool 26 in a first direction when control surface 3 is displaced in a first direction away from its failsafe position as shown in FIG. 10, and transmission mechanism 80 displaces valve arm 22 and metering spool 26 in a second and opposite direction when control surface 3 is displaced in a second and opposite direction away from its failsafe position as shown in FIG. 12. Transmission mechanism 80 may have any configuration providing desired kinematic response to displacement of control surface 3 away from its failsafe position such that valve arm 22 and metering spool 26 experience a corresponding intended displacement away from the null position. As may be understood, transmission mechanism 80 may include various types of gears, gear trains, links, linkage systems, and other transmission components to achieve a desired correspondence between the position of control surface 3 and metering spool 26. The transmission mechanism 80 shown in FIGS. 10-12 includes a control surface link 82 having a first end pivotally coupled to control surface 3 at pivot 82A spaced from hinge axis 11, and a second end 82B pivotally coupled to clevis 24. The configuration of transmission mechanism 80 shown in FIGS. 10-12 is merely for sake of illustration, and is not intended to limit the transmission mechanism to the configuration shown.

In the embodiment described above and depicted in the figures, metering spool 26 is rotatable about valve axis 25 in opposite rotational directions away from its null rotational position. However, those skilled in the art will understand that failsafe valve 20 may be designed such that metering spool 26 is movable axially along valve axis in opposite axially directions away from a null axial position to achieve similar functionality. For this type of modification, transmission mechanism 80 and valve arm 22 may be reconfigured such that angular motion of control surface 3 about hinge axis 11 is converted to linear motion which is transmitted to metering spool 26 to shift the axial position of the metering spool. For example, transmission mechanism may include a bell-crank linkage for converting angular motion to linear motion.

In an aspect of the present disclosure, the failsafe position of the actuated movable member (e.g. control surface 3) may be adjusted to suit different applications merely by reconfiguring transmission mechanism 80, without the need to make any structural modifications to failsafe valve 20 or to hydraulic rotary motor 12R. The failsafe position of the movable member need not be a centered position, and may be at or near a travel limit of its range of movement. This feature offers an important advantage over existing HITW designs of the prior art.

As will be appreciated, the present disclosure provides "HITW" failsafe functionality in an actuation system employing a hydraulic rotary actuator, such as hydraulically-powered flight control actuation system which employs GRAs powered by hydraulic rotary actuators instead of hydraulic linear actuators. The solution of the disclosure is easily adaptable to various different travel ranges and failsafe positions of the actuated member.

While the disclosure describes exemplary embodiments, the detailed description is not intended to limit the scope of the invention to the particular forms set forth. The invention is intended to cover such alternatives, modifications and equivalents of the described embodiment as may be apparent to one of ordinary skill in the art.

What is claimed is:

1. An actuation system for displacing a movable member relative to a fixed member, the movable member having a failsafe position and being displaceable away from the failsafe position, the actuation system comprising:
   an actuator connecting the movable member to the fixed member;
   a hydraulic system having a hydraulic supply line, a first hydraulic control line, a second hydraulic control line, and a hydraulic return line;
   a hydraulic rotary motor powered by the hydraulic system and arranged to drive the actuator to displace the movable member relative to the fixed member, the hydraulic rotary motor including a first control port in hydraulic communication with the first hydraulic control line, a second control port in hydraulic communication with the second hydraulic control line, and a return port in hydraulic communication with the hydraulic return line; and
   a failsafe valve in hydraulic communication with the hydraulic system and the hydraulic rotary motor, the failsafe valve being operably connected to the movable member;
   wherein the failsafe valve has a non-activated state when hydraulic pressure in the hydraulic supply line is greater than or equal to a predetermined normal pressure and an activated state when hydraulic pressure in the hydraulic supply line is less than the predetermined normal pressure;
   wherein, when the failsafe is in the non-activated state, the first hydraulic control line is in hydraulic communication with the first control port of the hydraulic rotary motor, the second hydraulic control line is in hydraulic communication with the second control port of the hydraulic rotary motor, and the return port of the hydraulic rotary motor is in hydraulic communication with the hydraulic return line, such that the hydraulic rotary motor operates normally;
   wherein, when the failsafe valve is in the activated state and the movable member is away from the failsafe position, the first hydraulic control line and the first control port of the hydraulic rotary motor, or the second hydraulic control line and the second control port of the hydraulic rotary motor, are in hydraulic communication with the hydraulic return line.

2. The actuation system according to claim 1, wherein the actuator is a geared rotary actuator defining a hinge axis, the movable member is angularly displaceable in opposite angular directions about the hinge axis relative to the fixed member, and the failsafe position is a predetermined angular position of the movable member about the hinge axis.

3. The actuation system according to claim 2, wherein the fixed member is a fixed wing of an aircraft, and the movable member is a control surface of the aircraft.

4. The actuation system according to claim 1,
   wherein the failsafe valve includes a command spool, a command port in hydraulic communication with the hydraulic supply line, a first control conduit in hydraulic communication with the first hydraulic control line and the first control port of the hydraulic rotary motor, a second control conduit in hydraulic communication with the second hydraulic control line and the second control port of the hydraulic rotary motor, and a return conduit in hydraulic communication with the hydraulic return line and the return port of the hydraulic rotary motor;
   wherein the command spool has a non-activated position in which the first control conduit and the second control conduit are not in hydraulic communication with the return conduit, and an activated position in which at least one of the first control conduit and the second control conduit is in hydraulic communication with the return conduit when the movable member is away from the failsafe position;
   wherein the command spool is biased toward the activated position;
   wherein the command spool is maintained in the non-activated position by hydraulic pressure in the hydraulic supply line when hydraulic pressure in the hydraulic supply line is greater than or equal to the predetermined normal pressure; and
   wherein the command spool is maintained in the activated position by biasing force when hydraulic pressure in the hydraulic supply line is less than predetermined normal pressure.

5. The actuation system according to claim 1,
wherein the failsafe valve includes a valve housing, a valve axis extending through the valve housing, and a metering spool movable relative to the valve housing;
wherein the metering spool is connected to the movable member such that a rotational position of the metering spool about the valve axis is determined by the position of the movable member relative to the fixed member; and
wherein the metering spool has a null rotational position about the valve axis corresponding to the failsafe position of the movable member.

6. The actuation system according to claim 5,
wherein the metering spool is rotatable about the valve axis in a first rotational direction away from the null rotational position for placing the first hydraulic control line and the first control port of the hydraulic rotary motor in hydraulic communication with the hydraulic return line when the failsafe valve is in the activated state; and
wherein the metering spool is rotatable about the valve axis in a second rotational direction opposite the first rotational direction away from the null rotational position for placing the second hydraulic control line and the second control port of the hydraulic rotary motor in hydraulic communication with the hydraulic return line when the failsafe valve is in the activated state.

7. The actuation system according to claim 5, wherein the metering spool is connected to the movable member by way of a transmission mechanism.

8. The actuation system according to claim 5, wherein the actuator is a geared rotary actuator defining a hinge axis, the movable member is angularly displaceable in opposite angular directions about the hinge axis relative to the fixed member, and the valve axis is parallel to the hinge axis.

9. The actuation system according to claim 1,
wherein the failsafe valve includes a valve housing, a valve axis extending through the valve housing, and a metering spool displaceable along the valve axis relative to the valve housing;
wherein the metering spool is connected to the movable member such that an axial position of the metering spool along the valve axis is determined by the position of the movable member relative to the fixed member; and
wherein the metering spool having a null axial position corresponding to the failsafe position of the movable member.

10. The actuation system according to claim 9,
wherein the metering spool is displaceable along the valve axis in a first axial direction away from the null axial position for placing the first hydraulic control line and the first control port of the hydraulic rotary motor in hydraulic communication with the hydraulic return line when the failsafe valve is in the activated state; and
wherein the metering spool is displaceable along the valve axis in a second axial direction opposite the first axial direction away from the null axial position for placing the second hydraulic control line and the second control port of the hydraulic rotary motor in hydraulic communication with the hydraulic return line when the failsafe valve is in the activated state.

11. The actuation system according to claim 9, wherein the metering spool is connected to the movable member by way of a transmission mechanism.

12. A method of operating an actuation system for displacing a movable member relative to a fixed member, the movable member having a failsafe position and being displaceable away from the failsafe position, the actuation system comprising an actuator connecting the movable member to the fixed member, a hydraulic system, and a hydraulic rotary motor powered by the hydraulic system and arranged to drive the actuator to displace the movable member relative to the fixed member, the method comprising:
A) providing a failsafe valve in hydraulic communication with the hydraulic system and the hydraulic rotary motor;
B) providing a mechanical connection between the failsafe valve and the movable member;
C) providing hydraulic communication between a first hydraulic control line of the hydraulic system and a first control port of the hydraulic rotary motor, between a second hydraulic control line of the hydraulic system and a second control port of the hydraulic rotary motor, and between a return line of the hydraulic system and a return port of the hydraulic rotary motor, when the hydraulic pressure in the hydraulic supply line is greater than or equal to a predetermined normal pressure; and
D) operating the failsafe valve by way of the mechanical connection to provide hydraulic communication between the first control port of the hydraulic rotary motor and the return line of the hydraulic system, or between the second control port of the hydraulic rotary motor and the return line of the hydraulic system, when the hydraulic pressure in the hydraulic supply line is less than or equal to the predetermined normal pressure and the movable member is away from the failsafe position.

13. The method according to claim 12, wherein the failsafe valve comprises a metering spool connected to the movable member by way of the mechanical connection, the metering spool having a null position corresponding to the failsafe position of the movable member, and the method further comprises adjusting the null position of the metering spool by changing the mechanical connection.

14. The method according to claim 12, wherein the actuator is a geared rotary actuator defining a hinge axis, the movable member is angularly displaceable in opposite angular directions about the hinge axis relative to the fixed member, and the failsafe position is a predetermined angular position of the movable member about the hinge axis.

15. The actuation system according to claim 14, wherein the fixed member is a fixed wing of an aircraft, and the movable member is a control surface of the aircraft.

16. The method according to claim 15, wherein step D comprises providing hydraulic communication between the first control port of the hydraulic rotary motor and the return line of the hydraulic system when the control surface is displaced from the failsafe position in a first angular direction, and providing hydraulic communication between the second control port of the hydraulic rotary motor and the return line of the hydraulic system when the control surface is displaced from the failsafe position in a second angular direction opposite the first angular direction.

\* \* \* \* \*